United States Patent [19]

Reissenweber et al.

[11] Patent Number: 5,428,174
[45] Date of Patent: Jun. 27, 1995

[54] PREPARATION OF α,β-UNSATURATED KETONES

[75] Inventors: Gernot Reissenweber, Boehl-Iggelheim; Winfried Richarz, Stockstadt, both of Germany

[73] Assignee: BASF Aktiengesellschaft, Ludwigshafen, Germany

[21] Appl. No.: 742,717

[22] Filed: Aug. 5, 1991

Related U.S. Application Data

[63] Continuation of Ser. No. 562,405, Jul. 20, 1990, abandoned, which is a continuation of Ser. No. 365,128, Jun. 12, 1989, abandoned.

[30] Foreign Application Priority Data

Jun. 23, 1988 [DE] Germany ............... 38 21 197.1

[51] Int. Cl.⁶ ............... C07D 261/08; C07D 335/02; C07D 309/04; C07C 45/00
[52] U.S. Cl. ............... 548/247; 549/13; 549/78; 549/427; 568/314; 568/346
[58] Field of Search ............ 549/78, 13, 427; 548/247; 568/314, 346, 388, 390

[56] References Cited

U.S. PATENT DOCUMENTS 3,846,497 11/1979 Himmele et al. ............ 260/592
4,355,184 10/1982 Kaku et al. ............ 568/388

FOREIGN PATENT DOCUMENTS

86/02065 4/1986 WIPO .

OTHER PUBLICATIONS

"Advanced Organic Chemistry" by Mar. pp. 835–837 (1985).
"Modern Synthetic reactions" by House pp. 224–229 (1965).
"Survey of organic Syntheses" by Buehler pp. 842–843 (1970).
"Orangic reactions" vol. 15 pp. 204–207 (1967).
"Handbook of Heterocyclic Chemistry" by Katritzky pp. 24–27, 125–130 (1985).
"Chem Sources–U.S.A" pp. 61, 49, 491–493 (1984).
Copy and Eundberg, Advanced Organic Chem. vol. A [New York: Plenum Press, 1984] pp. 332, 343.
Morrison and Boyd, Organic Chemistry, (Boston, Allyn and Bacon 1979), pp. 564–565.
European Search Report.
Organikum; Organisch–chemisches Grundpraktikum, pp. 466–468, VEB Deutscher, Berlin (1986).
Csaba Szantay und Janos Rohaly, Über die Bildung ungesattigter Ketone in den Mannich–Reaktionen substituierter Acetessigsauren, Chem. Ber., v. 96, pp. 1788–1791 (1963).

Primary Examiner—Jyothsna Venkat
Attorney, Agent, or Firm—Keil & Weinkauf

[57] ABSTRACT

α,β-Unsaturated ketones of the general formula I $$R-CH=CH-\overset{\overset{\displaystyle O}{\|}}{C}-CH_3 \qquad (I)$$

where R is an organic radical, are prepared by reacting a corresponding aldehyde R—CHO with acetoacetic acid or one of its salts in the presence of an amine in a two-phase reaction mixture by a process in which the reaction is carried out at a pH of from 6 to 8 in the presence of a catalytic amount of a primary amine.

2 Claims, No Drawings

PREPARATION OF α,β-UNSATURATED KETONES

This application is a continuation of application Ser. No. 562,405, filed on Jul. 20, 1990, which is a continuation of Ser. No. 365,128, filed on Jun. 12, 1989 both now abandoned.

The present invention relates to a process for the preparation of α,β-unsaturated ketones by reacting an aldehyde with acetoacetic acid or one of its salts in the presence of a primary amine.

DE-A-31 17 271 discloses a process for the preparation of α,β-unsaturated ketones of the general formula

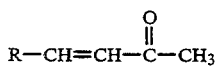

where R is an organic radical, by reacting a corresponding aldehyde R—CHO, which must have a hydrogen atom in the α-position, with acetoacetic acid or one of its salts, in which the reaction is carried out in the presence of a secondary, preferably nonaliphatic amine in a two-phase reaction mixture. In general, it is also known that certain condensation reactions of aldehydes take place satisfactorily only in the presence of secondary amines (Organikum, Berlin 1986, page 466, and Chem. Ber. 96 (1963), 1788 et seq.).

It is an object of the present invention to provide a process having a wider range of applications and to overcome the disadvantages of the process disclosed in DE-A-31 17 271.

We have found that this object is achieved, surprisingly, by a novel and improved process for the preparation of α,β-unsaturated ketones of the general formula I

where R is an organic radical, by reacting a corresponding aldehyde of the general formula R—CHO (II) with acetoacetic acid or one of its salts in a two-phase reaction mixture, wherein the reaction is carried out at a pH of from 6 to 8 in the presence of a catalytic amount of a primary amine of the general formula $R^1$—$NH_2$ (III), where $R^1$ is an organic radical.

The novel process is based on the following equation:

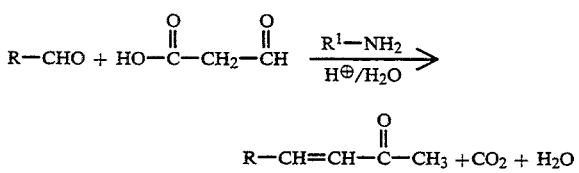

It can be seen that, in this process, the primary amine takes part in the reaction but is not consumed. Hence, a catalytic amount of in general less than 0.2, for example from 0.01 to 0.2, mole per mole of aldehyde is sufficient.

The reaction can be carried out as described below.

The aldehyde, in general in a solvent, and a catalytic amount of primary amine are added to an aqueous solution of the acetoacetic acid or of one of its salts, and if necessary the pH is brought to 6-8, preferably 6.2-7.2, by adding an acid. The solution is stirred at from 20° to 100° C., preferably from 30° to 80° C., until the reaction is complete (the preselected pH being maintained by continuously adding acid). In general, from 2 to 7 hours are adequate at a sufficiently high temperature. After the end of the reaction, which can be detected from the fact that the pH decreases when further acid is added, the pH is brought to 2 and the mixture is then worked up in a conventional manner. It may be advantageous to change the order of addition of the reactants, for example to add the aqueous solution of the acetoacetic acid or of one of its salts to the initially taken solution of the aldehyde or amine.

Suitable salts of acetoacetic acid are alkali metal or alkaline earth metal salts, such as the lithium, sodium, potassium or calcium salt. For example, commercial methyl acetoacetate can be used as the starting material.

Acetoacetic acid or its salt is obtained by hydrolyzing equimolar amounts of ethyl acetoacetate with an aqueous base, such as NaOH, KOH or $Na_2CO_3$; as a rule, alcohol liberated does not interfere with the further course of the reaction, and the mixture can thus be used directly for the novel process. For the preparation of α,β-unsaturated ketones which readily undergo an addition reaction with an alcohol under acidic conditions, it is advisable to remove the resulting alcohol after the hydrolysis, for example by distillation, and to use the aqueous acetoacetate solution, which is then alcohol-free.

Virtually any known aldehydes or aldehydes which can be prepared by general standard reactions (HoubenWeyl, Methoden der organischen Chemie, Vol. 7/2 (1954) and Vol. E3 (1983)) can be used as aldehydes II.

The molar ratio of acetoacetate to aldehyde is advantageously from 1:1 to 1.5:1, preferably from 1.1:1 to 1.3:1.

As a rule, it is advisable to use from 100 to 500 ml of a solvent which is advantageously immiscible with water per mole of aldehyde, this being essential if the aldehyde is a solid.

Examples of suitable substances are chlorohydrocarbons, such as methylene chloride, chloroform, carbon tetrachloride and dichloroethane, aromatic hydrocarbons, such as benzene, toluene and xylene, aromatic chlorohydrocarbons, such as chlorobenzene, and ethers, such as diethyl ether, methyl tert-butyl ether and diisopropyl ether.

Mineral acids, especially sulfuric acid and hydrochloric acid, are particularly suitable acids for regulating the pH.

If, in addition to the desired α,β-unsaturated ketone I, relatively large amounts of the corresponding β-hydroxyketone IV

are formed, 5 mol %, based on the aldehyde, of sulfuric acid can be added to the organic phase prior to distillation and the organic phase can be stirred for 2 hours at from 40° to 45° C. and then worked up in a conventional manner.

Among the primary amines III, preferred ones are those in which $R^1$ is straight-chain or branched $C_4$–$C_{20}$-alkyl, in particular $C_4$–$C_{12}$-n-alkyl, such as n-butyl, n-pentyl, n-hexyl, n-heptyl, n-octyl, n-decyl or n-dodecyl, straight-chain or branched $C_4$–$C_{20}$-alkenyl, in particular $C_4$–$C_{12}$-n-alkenyl, $C_4$–$C_{12}$-cycloalkyl, in particular $C_4$–$C_8$-cycloalkyl, such as cyclobutyl, cyclopentyl, cyclohexyl or cyclooctyl, $C_4$–$C_{20}$-alkylcycloalkyl, in particular $C_4$–$C_{12}$-alkylcycloalkyl, such as 2-methylcyclohexyl, $C_4$–$C_{20}$-cycloalkylalkyl, in particular $C_4$–$C_{12}$-cycloalkylalkyl, such as cyclopentylmethyl, cyclopentylethyl, cyclopentyl-n-butyl, cyclopentyl-n-hexyl, cyclohexylmethyl, cyclohexylethyl, cyclohexyl-n-butyl or cyclohexyl-n-hexyl.

Particularly suitable primary amines III are those in which $R^1$ is $C_4$–$C_{20}$-alkyl or $C_4$–$C_{20}$-alkenyl. This is particularly noteworthy since, according to DE-A-31 17 271, it is precisely aliphatic and cycloaliphatic amines which are supposed to be not very suitable.

Among the products I, preferred ones are those in which R is:

$C_4$–$C_{20}$-alkyl, in particular $C_4$–$C_8$-alkalkyl, such as methyl, ethyl, n-propyl, isopropyl, n-butyl, isobutyl, sec-butyl, tert-butyl or 2,6-dimethylheptyl, $C_2$–$C_{20}$-alkenyl, in particular $C_2$–$C_8$-alkenyl, $C_2$–$C_{20}$-alkynyl, in particular $C_2$–$C_8$-alkynyl, $C_2$–$C_{20}$-alkoxyalkyl, in particular $C_2$–$C_{12}$-alkoxyalkyl, such as methoxymethyl, $C_3$–$C_{20}$-alkoxyalkenyl, in particular $C_3$–$C_{12}$-alkoxyalkenyl, $C_3$–$C_{20}$-alkenyloxyalkyl, in particular $C_3$–$C_{12}$-alkenyloxyalkyl, $C_4$–$C_{20}$-alkenyloxyalkenyl, in particular $C_4$–$C_{12}$-alkenyloxyalkenyl, $C_2$–$C_{20}$-alkylthioalkyl, in particular $C_2$–$C_{12}$-alkylthioalkyl, such as 2-ethylthioprop-1-yl, $C_3$–$C_{20}$-alkylthioalkenyl, in particular $C_3$–$C_{12}$-alkylthioalkenyl, $C_3$–$C_{20}$-alkenylthioalkyl, in particular $C_2$–$C_{12}$-alkenylthioalkyl, $C_4$–$C_{20}$-alkenylthioalkenyl, in particular $C_3$–$C_{12}$-alkenylthioalkenyl, $C_3$–$C_{20}$-cycloalkyl, in particular $C_3$–$C_{12}$-cycloalkyl, such as cyclopropyl, cyclobutyl, cyclopentyl, cyclohexyl, cycloheptyl, cyclooctyl, cyclodecyl or cyclododecyl, $C_4$–$C_{20}$-alkylcycloalkyl, such as pinan-3-yl, $C_3$–$C_{20}$-cycloalkenyl, in particular $C_3$–$C_{12}$-cycloalkenyl, such as cyclododeca-4,8-dien-1-yl, $C_4$–$C_{20}$-alkylcycloalkenyl, such as 2-methylcyclohex-4-en-1-yl or 3,6,6-trimethylcyclohexa-1,3-dien-1-yl, $C_4$–$C_{20}$-bicycloalkyl, in particular $C_4$–$C_{12}$-bicycloalkyl, $C_5$–$C_{20}$-bicycloalkenyl, in particular $C_5$–$C_{12}$-bicycloalkenyl, aryl, such as phenyl, naphthyl or anthranyl, hetaryl, such as 2-pyrrolyl, 3-pyrrolyl, 2-pyridyl, 3-pyridyl or 4-pyridyl, aryl which is monosubstituted, disubstituted or trisubstituted by $C_4$–$C_8$-alkyl, in particular aryl which is monosubstituted, disubstituted or trisubstituted by $C_1$–$C_4$-alkyl, such as p-tolyl or 2,4,6-trimethylphenyl, aryl which is monosubstituted, disubstituted or trisubstituted by $C_1$–$C_8$-alkalkoxy, in particular aryl which is monosubstituted, disubstituted or trisubstituted by $C_1$–$C_4$-alkoxy, such as p-methoxyphenyl, aryl which is monosubstituted, disubstituted or trisubstituted by halogen, in particular aryl which is monosubstituted, disubstituted or trisubstituted by fluorine or chlorine, such as chlorophenyl, aryl which is monosubstituted, disubstituted or trisubstituted by cyano or nitro, hetaryl which is monosubstituted, disubstituted or trisubstituted by $C_1$–$C_8$-alkyl, in particular hetaryl which is monosubstituted, disubstituted or trisubstituted by $C_1$–$C_4$-alkyl, hetaryl which is monosubstituted, disubstituted or trisubstituted by $C_1$–$C_8$-alkalkoxy, in particular hetaryl which is monosubstituted, disubstituted or trisubstituted by $C_1$–$C_4$-alkoxy, hetaryl which is monosubstituted, disubstituted or trisubstituted by halogen, in particular hetaryl which is monosubstituted, disubstituted or trisubstituted by fluorine or chlorine, hetaryl which is monosubstituted, disubstituted or trisubstituted by cyano, hetaryl which is monosubstituted, disubstituted or trisubstituted by nitro, a saturated heterocyclic radical of 3 to 20, in particular 3 to 12, carbon atoms, such as thiophen-3-yl, tetrahydropyran-3-yl or tetrahydrothiopyran-3-yl, a saturated heterocyclic radical having 3 to 20 carbon atoms and an additional heteroatom from the group consisting of oxygen, sulfur and nitrogen, a saturated heterocyclic radical having 3 to 20 carbon atoms and two additional heteroatoms from the group consisting of oxygen, sulfur and nitrogen, an unsaturated heterocyclic radical having 3 to 20 carbon atoms, in particular a heterocyclic radical of 3 to 12 carbon atoms, an unsaturated heterocyclic radical having 3 to 20 carbon atoms and one additional heteroatom from the group consisting of oxygen, sulfur and nitrogen, such as 5,6-dihydro-4H-pyran-3-yl and 3-isopropyisoxazol-5-yl, an unsaturated heterocyclic radical having 3 to 20 carbon atoms and two additional heteroatoms from the group consisting of oxygen, sulfur and nitrogen.

The $\alpha,\beta$-unsaturated ketones I obtainable by the novel process are either end products (for example fragrance materials) or useful intermediates, for example for herbicidal active ingredients (DE-A-2 822 304, DE-A-2 439 104, DE-A-3 032 973, DE-A-3 047 924, DE-A-3 121 355 and EP-A-66 195).

EXAMPLE 1

Preparation of the keton
1-(3-tetrahydrothiopyranyl)-1-but-1-en-3-one

I. Preparation by the novel process a) 140 g (1 mole) of 30% strength sodium hydroxide solution are added dropwise to a mixture of 116.0 g (1 mole) of methyl acetoacetate in 140 ml of water in the course of about 60 minutes, after which stirring is carried out for about 5 hours at from 35° to 40° C. A yellowish clear solution of sodium acetoacetate is formed.

b) 100 g (0.77 mole) of thiopyran-3-carbaldehyde in 100 ml of toluene and 3.8 g (0.05 mole) of n-hexylamine are added to 396 g of the aqueous solution prepared in this manner and containing 1 mole of sodium acetoacetate, and the pH of the aqueous solution is brought to 6.2 by adding 40% strength sulfuric acid. The reaction mixture is then stirred at 50° C., the pH being kept constantly at 6.2–6.4 by the continuous addition of sulfuric acid. After the addition of 110 g of 40% strength sulfuric acid in the course of 90 minutes, stirring is continued for a further 30 minutes and the mixture is then acidified to pH 2. The aqueous phase is separated off and the organic phase is washed with water and evaporated down to give 125 g of a yellowish oil which has the following composition determined by gas chromatography:

2.2% of tetrahydrothiopyran-3-carbaldehyde
92.3% of 1-(3-tetrahydrothiopyranyl)-but-1-en-3-one
3.5% of 1-(3-tetrahydrothiopyranyl)-1-hydroxybutan-3-one.

Distillation gives 110 g of 1-(3-tetrahydrothiopyranyl)-but-1-en-3-one (compound 1; bp. 79°–81° C./0.2 mbar) in a purity of 98%. The yield is 84%, based on the aldehyde.

II. Preparation by the process according to DE-A-31 17 271 a) The reaction is carried out as in Example 1, Ib using di-n-butylamine, at a pH of from 6.0 to 6.5. After a reaction time of 8 hours, the organic phase has the following composition according to gas chromatographic analysis:

27.2% of tetrahydropyran-3-carbaldehyde
46.4% of 1-(3-tetrahydrothiopyranyl)-but-1-en-3-one
20.5% of 1-(3-tetrahydrothiopyranyl)-1-hydroxybutan-3-one.

b) When morpholine is used as the catalyst at pH 6.0–6.5, the following are obtained according to gas chromatographic analysis:

33.1% of tetrahydrothiopyran-3-carbaldehyde
9.7% of tetrahydropyran-3-carbaldehyde dimethyl acetal
32.4% of 1-(3-tetrahydropyranyl)-but-1-en-3-one
8.7% of 1-(3-tetrahydrothiopyranyl)-1-hydroxybutan-3-one.

c) When pyrrolidine is used as a catalyst at pH 6.5, the following are obtained according to gas chromatographic analysis:

48.4% of tetrahydrothiopyran-3-carbaldehyde
9.5% of tetrahydrothiopyran-3-carbaldehyde dimethyl acetal
29.9% of 1-(3-tetrahydrothiopyranyl)-but-1-en-3-one
2.3% of 1-(3-tetrahydrothiopyranyl)-1-hydroxybutan-3-one.

Compounds No. 2 to 11 listed in the Table below were prepared similarly to Example 1.

TABLE

| Compound No. | R | Prim. amine as catalyst | Molar ratio amine/aldehyde | Yield [%] | Physical data |
|---|---|---|---|---|---|
| 2 | Phenyl | n-Hexylamine | 0.03 | 91 | mp.: 35–39° C. |
| 3 | Phenyl | n-Dodecylamine | 0.05 | 88 | * |
| 4 | p-Chlorophenyl | n-Hexylamine | 0.05 | 95 | mp.: 50–57° C. |
| 5 | p-Methoxyphenyl | n-Pentylamine | 0.075 | 89 | mp.: 70–71° C. |
| 6 | p-Tolyl | n-Heptylamine | 0.05 | 95 | * |
| 7 | Thiophen-3-yl | n-Hexylamine | 0.05 | 98 | mp.: 61–64° C. |
| 8 | (isobutyl-substituted isoxazoline structure) | n-Hexylamine | 0.05 | 90 | $^1$H-NMR (CDCl$_3$): 1,35 d (6H), 2,4 s (3H) 3,1: m (1H), 6,5 s (1H) 6,8 d (1H), 7,35 d (1H) |
| 9 | Cyclohexyl | n-Heptylamine | 0.045 | 86 | Kp.: 50–55° C./0,3 mbar |
| 10 | 4-Methylcyclohexyl | n-Hexylamine | 0.05 | 88 | $^1$H-NMR (CDCl$_3$): 1,95 d (3H), 1, 0-2, 2m (10H), 2,3 s (3H), 6,05 d (1H), 6,8 dd (1H) |
| 11 | sec.-Butyl | n-Hexylamine | 0.05 | 75 | $^1$H-NMR (CDCl$_3$): 1,9 d (6H), 2,8 m (1H), 2,1 t (2H), 2,25 s (3H), 6,1 d (1H) 6,8 m (1H) |

Detected by GC

EXAMPLE 2

1-(3-Tetrahydrothiopyranyl)-but-1-en-3-one

When the reaction is carried out similarly to Example 1,I but at a pH of 7.0 to 7.2, the organic phase obtained is found to have the following composition according to gas chromatographic analysis:

2.8% of tetrahydrothiopyran-3-carbaldehyde
80.7% of 1-(3-tetrahydrothiopyranyl)-but-1-en-3-one
11.3% of 1-(3-tetrahydrothiopyranyl)-1-hydroxybutan-3-one.

3.5 g of concentrated sulfuric acid are added to the toluene phase and the mixture is stirred for 2 hours at from 40° to 45° C. It is then extracted with water and the toluene is evaporated off. 128 g of a crude product having the following composition (GC) are obtained:

2.6% of tetrahydropyran-3-carbaldehyde
89.3% of 1-(3-tetrahydrothiopyranyl)-but-1-en-3-one
1.2% of 1-(3-tetrahydrothiopyranyl)-1-hydroxybutan-3-one.

We claim:

1. A process for the preparation of an α,β-unsaturated ketone of the formula I

where R is an organic radical, by reacting an aldehyde of the formula II

with acetoacetic acid or one of its salts in the presence of an amine in a two-phase reaction mixture, wherein the reaction is carried out at a pH of from 6 to 8 in the presence of a catalytic amount of primary amine of the formula $$R^1-NH_2 \qquad (III)$$

where $R^1$ is a straight-chain or branched $C_4$–$C_{20}$-alkyl or a straight-chain or branched $C_4$–$C_{20}$-alkenyl.

2. A process for the preparation of an α,β-unsaturated ketone I as defined in claim 1, wherein R is $C_1$–$C_{20}$-alkyl, $C_2$–$C_{20}$-alkenyl, $C_2$–$C_{20}$-alkynyl, $C_2$–$C_{20}$-alkoxyalkyl, $C_3$–$C_{20}$-alkoxyalkenyl, $C_3$–$C_{20}$-alkenyloxyalkyl, $C_4$–$C_{20}$-alkenyloxyalkenyl, $C_2$–$C_{20}$-alkylthioalkyl, $C_3$–$C_{20}$-alkylthioalkenyl, $C_3$–$C_{20}$-alkenylthioalkyl, $C_4$–$C_{20}$-alkenylthioalkenyl, $C_3$–$C_{20}$-cycloalkyl, $C_3$–$C_{20}$-cycloalkenyl, $C_4$–$C_{20}$-bicycloalkyl, $C_5$–$C_{20}$-bicycloalkenyl, aryl, hetaryl, aryl or hetaryl which is monosubstituted to trisubstituted by $C_4$–$C_8$-alkyl, $C_1$–$C_8$-alkoxy, halogen, cyano or nitro, or a saturated or unsaturated heterocyclic radical of 3 to 20 carbon atoms which contains from one to three heteroatoms from the group consisting of oxygen, sulfur and nitrogen.

* * * * *

UNITED STATES PATENT AND TRADEMARK OFFICE
CERTIFICATE OF CORRECTION

PATENT NO.: 5,428,174

DATED: June 27, 1995

INVENTOR(S): REISSENWEBER et al.

It is certified that error appears in the above-identified patent and that said Letters Patent is hereby corrected as shown below:

Column 8, claim 2, line 6, "$C_4$-$C_8$-" should be -- $C_1$-$C_8$- --.

Signed and Sealed this

Twenty-ninth Day of August, 1995

*Attest:*

BRUCE LEHMAN

*Attesting Officer*     *Commissioner of Patents and Trademarks*